United States Patent [19]
Adams et al.

[11] Patent Number: 5,674,253
[45] Date of Patent: Oct. 7, 1997

[54] CARDIOVERSION SYSTEM WITH CARDIOVERTING ENERGY ATTENUATOR

[75] Inventors: John M. Adams, Issaquah; Clifton A. Alferness, Redmond; Darrell O. Wagner, Gold Bar, all of Wash.

[73] Assignee: InControl, Inc., Redmond, Wash.

[21] Appl. No.: 708,218

[22] Filed: Sep. 6, 1996

[51] Int. Cl.$^6$ ........................................ A61N 1/39
[52] U.S. Cl. ................................. 607/7; 607/63
[58] Field of Search ........................... 607/5, 7, 63

[56] References Cited

U.S. PATENT DOCUMENTS

| | | | |
|---|---|---|---|
| 3,653,387 | 4/1972 | Ceier | 607/5 |
| 3,866,615 | 2/1975 | Hewson | 607/7 |
| 5,403,353 | 4/1995 | Alferness et al. | 607/5 |
| 5,433,732 | 7/1995 | Hirschberg et al. | 607/7 |
| 5,484,452 | 1/1996 | Persson | 607/5 |

*Primary Examiner*—William E. Kamm
*Assistant Examiner*—Kennedy J. Schaetzle
*Attorney, Agent, or Firm*—Richard O. Gray, Jr.

[57] ABSTRACT

A defibrillation system for providing post-cardiac surgery atrial cardioversion includes a lead system having defibrillation electrodes for electrical contact with the heart beneath the skin of a patient and a non-implantable external defibrillator for providing defibrillation electrical energy. An interface unit is coupled between the external defibrillator and the lead system and includes an attenuator circuit for attenuating the defibrillation electrical energy provided by the external defibrillator.

15 Claims, 2 Drawing Sheets

CARDIOVERSION SYSTEM WITH CARDIOVERTING ENERGY ATTENUATOR

BACKGROUND OF THE INVENTION

The present invention is generally directed to a cardioverting system for providing temporary cardioversion of a heart surgery patient following a heart surgery procedure. The present invention is more particularly directed to an energy attenuator for use in such cardioverting systems to enable virtually any external defibrillator to be safely used in such systems.

There are approximately four hundred thousand (400,000) heart surgery procedures performed annually in the United States. The types of such surgical procedures vary from coronary artery bypass grafts to valve replacements, to repair of congenital heart defects. In order to gain access to the heart, most of these surgeries require the chest to be opened in the middle of the sternum. An incision is then made in the pericardial sac (pericardium) to expose the heart and permit the required surgical procedure to be performed. Following the surgical procedure, the pericardial incision is reapproximated (closed except for a drain opening) with sutures and the chest cavity is closed.

Often, during recovery following such heart surgical procedures, the patients'hearts experience an arrhythmia called atrial fibrillation during the immediate or early post-surgical period. When this occurs, the heart beats rapidly and irregularly. According to reports, this constitutes a major clinical problem resulting in hypotension, heart failure, pneumonia and/or stroke, due to thromboembolism. Hence, such a condition is of great concern to the physician and it is therefore in the best interest of the patient to terminate this arrhythmia as soon as possible.

The development of post-surgical atrial fibrillation has not been clearly associated with preoperative or postoperative clinical predictors. Further, the specificity and sensitivity of age and other possible relevant factors for prediction of atrial fibrillation after heart surgery is low. No effective prophylactic regimen has yet been established.

When atrial fibrillation of a surgical patient's heart occurs during surgery, the physician terminates the fibrillation by cardioverting the heart. In this cardioversion procedure, the physician contacts each atria with a spoon-sized conductive paddle which is coupled to an external defibrillator. The external defibrillator includes a storage capacitor which is charged to a selected voltage. When the storage capacitor is fully charged, the stored energy is discharged into the atria of the heart through the paddles.

While the above-mentioned cardioverting process is very effective in terminating atrial fibrillation occurring during surgery, this procedure is not available to the physician for terminating atrial fibrillation occurring after the heart surgery is completed and the patient's chest cavity has been closed. It has been observed that the peak incidence of atrial fibrillation is up to the seventh postoperative day. While external cardioversion is an option, because the patient's chest cavity at this time is closed, much larger paddles and much greater cardioverting energies must be used as compared to the paddle size and cardioverting energies employed during surgery. Such energies, generally between 50 and 360 joules, would also require the patient to be briefly anesthetized or sedated prior to attempted external cardioversion. Hence, while external cardioversion, using much larger paddles and much higher cardioverting energies, is available to the physician as an option, most physicians would prefer to avoid such external cardioversion because of the likely trauma and tissue damage it would cause the patient during a time in which the patient is in a critical initial recovery phase from open heart surgery.

Drug therapy is also an available option. Its use however is often attended with ineffectiveness, potential harm and significant side effects. In addition, there is a substantial potential interaction of such drugs with the many different types and amounts of other drugs the patient is already receiving during this initial recovery period.

U.S. Pat. No. 5,403,353 discloses one cardioverting system and method capable of arresting fibrillation, such as atrial fibrillation, occurring during the post-heart surgery period. The system and method there disclosed does not cause prolongation of the patient's recovery period due to trauma and tissue damage and avoids the need for drug therapy to treat such a condition. To accomplish this end, a pair of temporary leads are releasably anchored beneath the skin of the patient during the open chest surgical procedure. Each lead is provided with an elongated electrode which is disposed in electrical contact with one of the atria. The temporary leads are then available to apply comparatively low voltage cardioverting energy to the atria when the atria are in need of cardioversion. When the leads are no longer needed, they can be pulled from the patient's body.

For providing the cardioversion energy during the post-surgery period, a standard external defibrillator is the logical choice. Every hospital having cardiac surgery facilities has multiple, readily available, external defibrillators. However, such defibrillators are capable of providing up to 360 joules of energy. Such energies are excessive for this application and more importantly, would be unsafe if applied directly beneath the skin of the patient.

The present invention is therefore directed to a cardioverting system which renders the use of standard external defibrillators both safe and convenient for internal cardioversion applications. More specifically, the system includes an interface unit between the external defibrillator and the temporary defibrillation leads which includes an attenuator for attenuating the defibrillator output energy to a safe level even when the defibrillator is set to provide maximum output. Other safety features are provided which will become apparent hereinafter.

SUMMARY OF THE INVENTION

The invention provides a defibrillation system including a lead system having defibrillation electrodes for electrical contact with a heart beneath the skin of a patient, a nonimplantable external defibrillator for providing defibrillation electrical energy, and interface means coupled between the external defibrillator and the lead system and including attenuating means for attenuating the defibrillation electrical energy provided by the external defibrillator.

The external defibrillator may include a pair of paddles for delivering the defibrillation electrical energy, and the interface means may include a pair of conductive surfaces for receiving the paddles and hence the defibrillation electrical energy.

The invention further provides an interface unit for use in a defibrillation system having a lead system including defibrillation electrodes for electrical contact with a heart beneath the skin of a patient and a nonimplantable external defibrillator capable of providing, across a pair of outputs, electrical energy having magnitudes unsafe if applied directly to the defibrillation electrodes. The interface unit has inputs for coupling to the external defibrillator outputs, outputs for coupling to the defibrillation electrodes, and attenuating means coupled between the inputs and outputs for attenuating the electrical energy provided by the external defibrillator.

BRIEF DESCRIPTION OF THE DRAWINGS

The features of the present invention which are believed to be novel are set forth with particularity in the appended claims. The invention together with further objects and advantages thereof may best be understood by making reference to the following description taken in conjunction with the accompanying drawings in the several figures of which like reference numerals identify like elements, and in:

DETAILED DESCRIPTION

Figure 1:
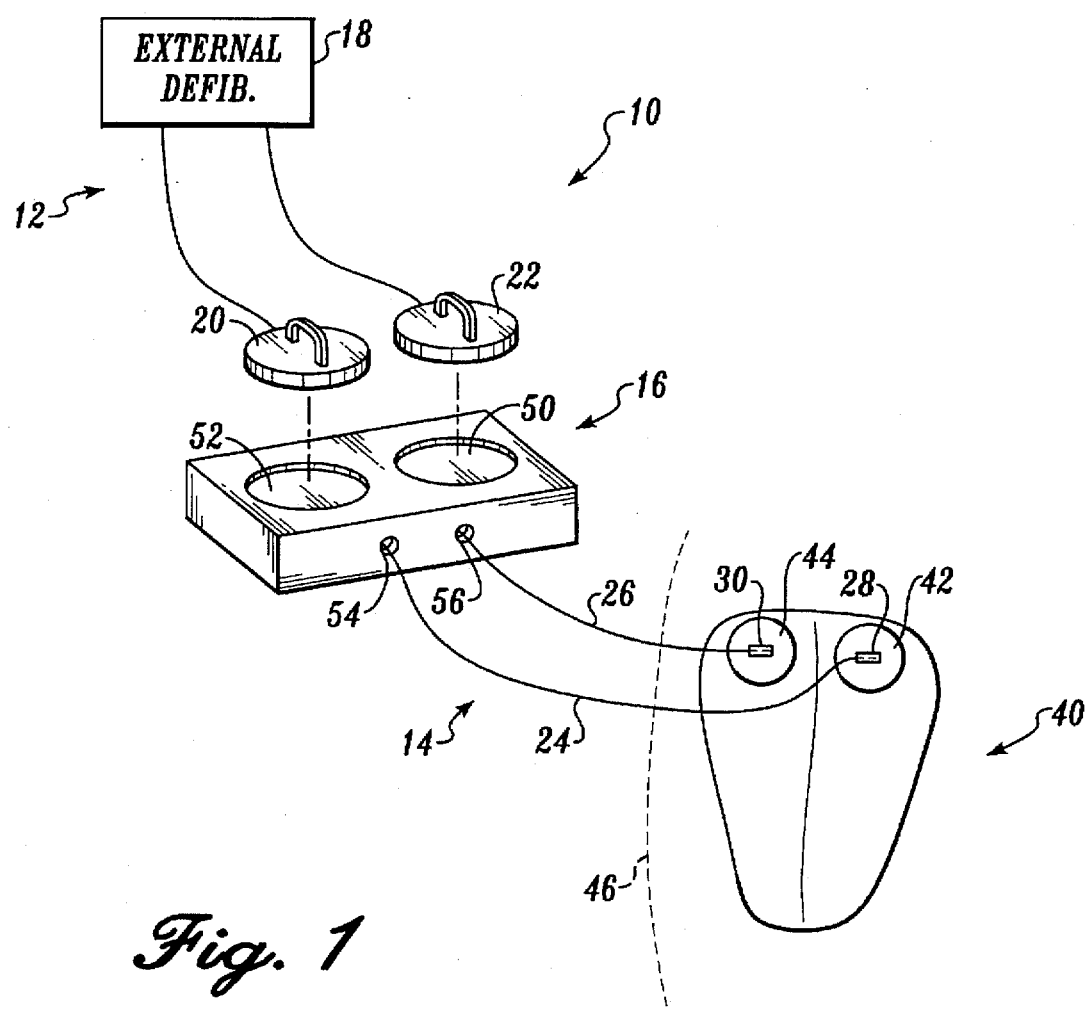
FIG. 1 is an exploded prospective view of a defibrillation system 10 embodying the present invention which includes an external defibrillator, a lead system, and an interface unit for coupling the external defibrillator to the lead system in accordance with the present invention.

Referring now to FIG. 1, it illustrates a defibrillation system 10 embodying the present invention. The defibrillation system 10 generally includes an external defibrillator 12, a lead system 14, and an interface unit 16. The interface unit 16, in accordance with the present invention, couples the external defibrillator 12 to the lead system 14.

The external defibrillator 12 includes a cabinet or housing 18 which encloses electrical circuitry (not shown) for generating cardioverting or defibrillating electrical energy. Preferably, the external defibrillator 18 is of the type well known in the art which is capable of providing cardioverting or defibrillating electrical energy on the order of up to 360 joules, for example. Such energies are commonly utilized for external cardioversion. To that end, the external defibrillator 18 includes a pair of output defibrillation paddles with which, during external cardioversion, the cardioverting or defibrillating electrical energy from the external defibrillator 18 is applied to a patient's chest.

The lead system 14 preferably includes a first lead 24 and a second lead 26 which terminate, at their distal ends, with elongated defibrillation electrodes 28 and 30 respectively. Such a lead system is fully described in the aforementioned U.S. Pat. No. 5,403,353 which is assigned to the assignee of the present invention and incorporated herein by reference. In accordance with the teachings of that patent, the defibrillation electrodes 28 and 30 are in electrical contact with a heart 40. More specifically, the electrodes 28 and 30 are in electrical contact with the left atrium 42 and right atrium 44 respectively of the heart 40. The electrodes 28 and 30 establish electrical contact with the heart beneath the skin of the patient represented by the dashed line 46.

To successfully cardiovert or defibrillate the atria, electrical cardioverting energy having magnitudes up to about 9 joules, for example, will be sufficient when applied between the electrodes 28 and 30. The electrodes 28 and 30, by virtue of their dimension and the proximity to the heart, impose a potential hazard if defibrillating energies capable of being delivered by the external defibrillator 18 were applied directly across the electrodes 28 and 30. Such excessive energies could cause injury to the atria of the heart 40 and, in the least, burning of atrial tissue. As a result, external defibrillators customarily found in cardiac wards of hospitals would be unsuitable for direct application with the lead system 14. However, such external defibrillators are readily available in essentially every cardiac ward and hence would be the source of choice for providing the cardioverting electrical energy to cardiovert atrial fibrillation during the post-surgery period.

The interface unit 16 renders the use of standard external defibrillators such as external defibrillator 18 both safe and convenient. To facilitate convenience, the interface unit 16 includes a pair of conductive surfaces or contacts 50 and 52 dimensioned for receiving the output paddles 20 and 22 of the external defibrillator 18. This permits the cardioverting electrical energy provided by the external defibrillator 18 to be applied to the interface unit 16. The interface unit 16 further includes a pair of output terminals 54 and 56 which are coupled to the leads 24 and 26, and thus the electrodes 28 and 30 respectively of the lead system 14. As will be seen hereinafter, the interface unit 16 includes an attenuating circuit which attenuates the electrical energy provided by the external defibrillator 18 to a safe level to be applied to the electrodes 28 and 30 of the lead system 14.

Figure 2:
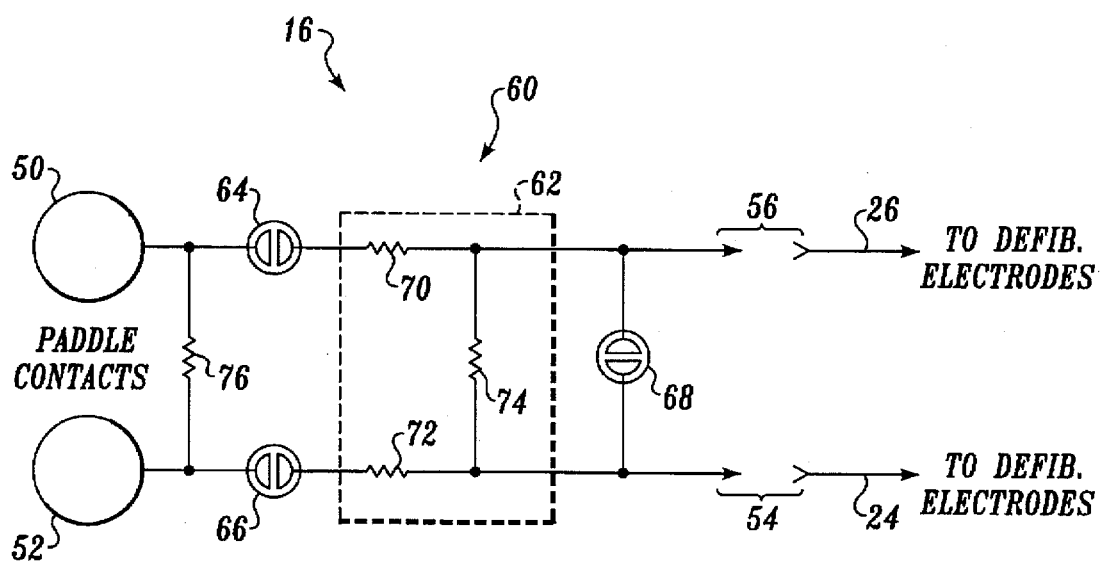
FIG. 2 is a schematic circuit diagram illustrating a manner in which the interface unit of FIG. 1 may be implement in accordance with a preferred embodiment of the present invention.

Referring now to FIG. 2, it illustrates the manner in which the interface unit 16 may be implemented to provide the aforementioned attenuation. The circuit 60 of interface unit 16 includes an attenuation circuit 62 and surge arresters 64, 66, and 68. Also illustrated in FIG. 2 are the conductive contacts 52 and 50 arranged to receive the paddles 20 and 22 of the external defibrillator 18 and the connectors 54 and 56 which couple the interface unit to electrodes 28 and 30 of leads 24 and 26.

The attenuating circuit 62 preferably comprises a resistive divider network including resistors 70, 72, and 74. The values of the resistors 70, 72, and 74 are preferably selected so that the impedance seen at the paddle contacts 50 and 52 is approximately 50 ohms while attenuating the energy applied to the paddle contacts 50 and 52 by the external defibrillator 18 by approximately 97.5%. As a result, the energy provided at the output connectors 54 and 56 of the interface unit 16 will be approximately 2.5% of the energy applied by the external defibrillator 18 at the paddle contacts 50 and 52. This represents a reduction of the electrical energy provided by the external defibrillator 18 by a factor of approximately 40. As a result, if the external defibrillator is set to provide output energy of 360 joules, the energy applied to the electrodes 28 and 30 will be approximately 9 joules.

To achieve the foregoing operation, resistors 70 and 72 may have a resistance of 20 ohms and resistor 74 may have a resistance of 15 ohms. The resistors 70, 72, and 74 are also preferably capable of dissipating 100 watts of power with a maximum working voltage of 2.0 KV.

The surge arresters 64 and 66 are disposed in series with the paddle contacts 50 and 52 respectively and hence are disposed for being in series with the output paddles 22 and 20 respectively of the external defibrillator 18. The surge arresters form a current limiter to prevent leakage currents from inadvertently being applied to the electrodes 28 and 30 of the lead system 14. To that end, the surge arresters each preferably have a conduction voltage of approximately 500 volts so that in order to apply any energy to the electrodes 28 and 30, a voltage of at least 1000 volts would be required across the paddle contacts 50 and 52 and hence across the output paddles 22 and 20 of the external defibrillator 18. This would correspond to an energy of approximately 20 joules being provided by the external defibrillator 18 and, after attenuation by the interface unit 16, 0.5 joules being applied to the atria 28 and 30 of the heart 40.

The surge arrester 68 is arranged for coupling between the leads 24 and 26 of the lead system 14 and hence between the electrodes 28 and 30. The surge arrester 68 preferably has a conduction voltage of approximately 1000 volts. It is provided to impose a short circuit path between the electrodes 28 and 30 should the resistor 74 fail in operation and present an open circuit or if one of the resistors 70 or 72 fails in a short circuit condition. By virtue of the surge arrester 68 being disposed between the electrodes 28 and 30, the heart will be protected should any of the resistors 70, 72, and 74 fail as described above. Another resistor 76 may be provided as shown to prevent the surge arresters 70 and 72 from conducting at applied voltages below their thresholds.

In operation, after the cardiac surgery procedure is performed, the electrodes 28 and 30 are placed beneath the skin of the patient so as to be in electrical contact with the atria 42 and 44 respectively. Should the patient during the post-surgical period develop atrial fibrillation, the leads 24 and 26 would then be connected to the output connectors 54 and 56 of the interface unit 16. The external defibrillator 18 can then be set to provide the desired quantity of cardioverting electrical energy and the paddles 22 and 20 brought into contact with the paddle contacts 50 and 52 of the interface unit 16. When the external defibrillator 18 provides the defibrillating electrical energy, the interface unit 16 attenuates the energy as previously described for providing the appropriate amount of energy to the electrodes 28 and 30 for safely cardioverting the atria 42 and 44.

As a result, atrial cardioversion during the post-surgery period is rendered safe with a conventional external defibrillator as shown in FIG. 1. The use of the conventional external defibrillator is also rendered convenient by virtue of the output paddles 20 and 22 being directly usable to engage paddle contacts 50 and 52 of the interface unit 16. As a result, for this application, the external defibrillator 18 need not be modified in any way in order to appropriately and successfully cardiovert the atria of a patient during the post-surgery period. Lastly, the use of a conventional external defibrillator for post-surgery atrial fibrillation cardioversion is rendered even more safe by virtue of the surge arresters 64, 66 and 68. As previously mentioned, surge arresters 64 and 68 prevent leakage currents from being applied to the atria of the heart and surge arrester 68 prevents inadvertent application of all of the output of the external defibrillator 18 should resistor 74 fail in an open circuit condition as can be appreciated from the foregoing unit, the interface of the present invention may be used to advantage whenever temporary leads are to be used for cardioversion. As a result, the present invention is directed to a broad range of applications.

While a particular embodiment of the present invention has been shown and described, modifications may be made, and it is therefore intended to cover in the appended claims all such changes in modifications which fall within the true spirit and scope of the invention.

What is claimed is:

1. A defibrillation system comprising:
   lead means having defibrillation electrodes for electrical contact with a heart beneath the skin of a patient;
   a nonimplantable external defibrillator for providing defibrillation electrical energy; and
   interface means coupled between the external defibrillator and the lead means and including attenuating means for attenuating the defibrillation electrical energy provided by the external defibrillator.

2. A system as defined in claim 1 wherein the attenuating means comprises a resistive divider network.

3. A system as defined in claim 1 wherein the external defibrillator includes at least one output and wherein the interface means includes a current limiter disposed in series with the at least one output.

4. A system as defined in claim 3 wherein the current limiter includes a surge arrester.

5. A system as defined in claim 3 wherein the external defibrillator includes a pair of outputs and wherein the current limiter comprises a pair of surge arresters disposed within the interface means, each respective surge arrester being disposed in series with a corresponding one of the outputs.

6. A system as defined in claim 1 wherein the lead means includes at least two defibrillation electrodes and wherein the interface means includes surge arrester means coupled between the at least two defibrillation electrodes.

7. A system as defined in claim 6 wherein the surge arrester means comprises a surge arrester.

8. A system as defined in claim 1 wherein the external defibrillator includes a pair of paddles for delivering the defibrillation electrical energy, and wherein the interface means includes a pair of conductive surfaces for receiving the paddles and the defibrillation electrical energy.

9. In a defibrillation system having a lead system including defibrillation electrodes for electrical contact with a heart beneath the skin of a patient and a nonimplantable external defibrillator capable of providing, across a pair of outputs, electrical energy having magnitudes unsafe if applied directly to the defibrillation electrodes, the improvement of an interface unit having inputs for coupling to the external defibrillator outputs, outputs for coupling to the defibrillation electrodes, and attenuating means coupled between the inputs and outputs for attenuating the electrical energy provided by the external defibrillator.

10. A unit as defined in claim 8 wherein the attenuating means comprises a resistive divider network.

11. A unit as defined in claim 9 further including a current limiter disposed for being in series with at least one of the external defibrillator outputs.

12. A unit as defined in claim 11 wherein the external defibrillator includes a pair of outputs and wherein the current limiter comprises a pair of surge arresters, each respective surge arrester being disposed for being in series with a corresponding one of the external defibrillator outputs.

13. A unit as defined in claim 9 wherein the lead system includes at least two defibrillation electrodes and wherein the interface unit includes surge arrester means disposed for being coupled between the at least two defibrillation electrodes.

14. A unit as defined in claim 13 wherein the surge arrester means comprises a surge arrester.

15. A unit as defined in claim 9 wherein the external defibrillator includes a pair of paddles for delivering the electrical energy, and wherein the interface means inputs includes a pair of conductive surfaces for receiving the paddles and the external defibrillator electrical energy.

* * * * *